United States Patent [19]

Salatinjants

[11] Patent Number: 4,716,173

[45] Date of Patent: Dec. 29, 1987

[54] METHOD OF TREATMENT OF MALARIA BY ONE TIME INTERFERENCE

[76] Inventor: Aida Salatinjants, 1333 N. Hobart, Los Angeles, Calif. 90027

[21] Appl. No.: 698,837

[22] Filed: Feb. 6, 1985

[51] Int. Cl.⁴ .................. A61K 31/47; A61K 31/715; A61K 31/525; A61K 31/34
[52] U.S. Cl. ..................................... 514/314; 514/54; 514/251; 514/461; 514/558; 514/567; 514/574; 514/895
[58] Field of Search ..................... 424/195.1; 514/314, 514/251, 558, 54, 574, 461, 567

[56] References Cited

PUBLICATIONS

Merck Index 9th ed., 1976, No. 2276, and 7853.

*Primary Examiner*—J. R. Brown
*Assistant Examiner*—John W. Rollins, Jr.
*Attorney, Agent, or Firm*—Joseph E. Mueth

[57] ABSTRACT

A composition adapted to prolong the residence time of sulfa and cinchona alkaloid drugs in the circulating plasma of mammals including humans comprising hexanoic acid, potassium hydrogen tartrate, tannic acid, pectin and riboflavin, with the further presence of glutamic acid in the case of sulfa drugs and L-tyrosine in the case of the cinchona alkaloids.

4 Claims, No Drawings

METHOD OF TREATMENT OF MALARIA BY ONE TIME INTERFERENCE

BACKGROUND OF THE INVENTION

The clinical pharmacology of the sulfonamides is generally characterized by the following. A single 2.0 gram dose of sulfisoxazole results in a mean time of peak plasma concentration of 2.5 hours. About 97% of the original dose is excreted in the urine within 48 hours. The mean elimination half life is 5.8 hours, ranging from 4.6 to 7.8 hours. These characteristics are typical of the other "sulfa"-type drugs such as sulfamethizone, sulfamethoxazole and sulfasalazine.

In the case of quinine, its salts, and the other cinchona alkaloids, peak plasma concentrations occur within 1 to 3 hours after a single oral dose of 260 mg in the form of the sulfate. The half-life is 4 to 5 hours. After termination of quinine therapy, the plasma level falls rapidly and is barely detectable after 24 hours.

The present invention relates to the treatment of diseases caused by bacterial and viral infections such as malaria, dysentery and the like.

The present day treatment of such diseases requires the repeated administration of the appropriate drug to the patient, for example, quinine in the case of malaria, and sulfathiazole in the case of dysentery. The need for repeated administration is due to the fact that the drug is rapidly eliminated from the circulating plasma and the body, as noted above. Rapid elimination of the drug significantly increases the complexity of treatment and prolongs it. Repeated administration is not always effective, and the process of the repeated administration makes more complicated the organization of the drug and works negatively on the psychology of the patient.

Increasing the residence time of a drug within the patient prolongs the effect of the drug, provides more uniform plasma levels, and reduces the number and frequency of side effects.

The present invention provides for the prolongation of the efficacy of the drug in mammals including humans by prolonging the plasma residence time.

By the practice of this invention, a single administration of a drug such as quinine dihydrochloride and sulfathiazole persists in the blood plasma up to 28-30 days. It is believed that the present invention represents a major advance in pharmacology and that it will be widely adapted by those skilled in the art.

SUMMARY OF THE INVENTION

Briefly, the present invention comprises a composition adapted to prolong the residence time of sulfa and cinchona alkaloid drugs in the circulating plasma of mammals including humans comprising hexanoic acid, potassium hydrogen tartrate, tannic acid, pectin and riboflavin, with the further presence of glutamic acid in the case of sulfa drugs, and L-tyrosine in the case of the cinchona alkaloids.

The essential ingredients are tannic acid, pectin, potassium hydrogen tartrate and L-tyrosine for the antimalarials, and tannic acid, pectin, potassium hydrogen tartrate and glutamic acid for the sulfonamides.

The invention also preferably comprehends the method of treating dysentery which comprises administering to a mammal suffering dysentery an effective amount of a composition comprising a sulfa drug, hexanoic acid, potassium hydrogen tartrate, tannic acid, pectin, riboflavin and glutamic acid.

The invention further preferably includes the method of treating malaria which comprises administering to a mammal suffering malaria an effective amount of a composition comprising a cinchona alkaloid drug, hexanoic acid, potassium hydrogen tartrate, tannic acid, pectin, riboflavin and L-tyrosine.

It is an object of the present invention to provide an improved therapuetic composition.

More particularly, it is an object of this invention to provide a means of prolonging the residence time of drugs in the circulating plasma of mammals.

These and other objects and advantages of this invention will appear from the following more detailed description.

DESCRIPTION OF THE PREFERRED EMBODIMENTS

A. ANIMAL STUDIES

METHOD

Sample Preparation:

Quinine solutions were mixed immediately prior to dosing the animals. Group I (control) was 25 mg of quinine dihydrochloride (K&K, Lot No. 26985-A) dissolved in 1.03 ml water. Group II was 25 mg of the quinine dihydrochloride dissolved in 1.03 ml of Drug No. 1. Group III was 25 mg of the quinine dihydrochloride dissolved in 4.86 ml of Drug No. 2.

| The composition of Drug No. 1 was: | |
|---|---|
| Hexanoic Acid | 0.06 grams |
| Tannic Acid | 0.08 grams |
| Pectin | 0.94 grams |
| Riboflavin 10% | 2.00 grams |
| Water to make 67 ml. | |
| The composition of Drug No. 2 was: | |
| Hexanoic Acid | 0.06 grams |
| Tannic Acid | 0.08 grams |
| Pectin | 0.94 grams |
| Riboflavin 10% | 2.00 grams |
| Potassium Hydrogen Tartrate | 0.48 grams |
| L-Tyrosine | 0.21 grams |
| Water to make 316 ml. | |

Procedure:

Six male Sprague-Dawley rats weighing between 200-300 gm were used. Two rats (Group I were injected intramuscularly at a dosage level of 1.03 ml/kg body weight with the quinine dihydrochloride water solution. Two rats (Group II) were injected intramuscularly at a dosage of 1.03 ml/kg body weight with the quinine dihydrochloride plus drug No. 1 solution. Two rats (Group III) were dosed orally at a dosage level of 4.86 ml/kg body weight with the quinine dihydrochloride plus drug No. 2 solution (See Table I). Dosage levels were rounded up to the nearest tenth.

Blood samples were taken from Group I at 30 minutes following injection. Blood samples were taken from Groups II and III at 24 hours following dosing. Plasmas were prepared, pooled in equal volumes and sent for quinine determination by high performance thin layer chromatography at National Medical Services, Willowgrove, Pa. The pooling schedule and results are presented in Table II.

TABLE I

| Group # | Animal # | Animal Weight | Dosage Level | Dose | Route of Admin. | Time of Sacrifice |
|---|---|---|---|---|---|---|
| I (Quinine Control) | 1 | 286 gm | 1.03 ml/kg | 0.3 ml | IM | 30 minutes |
|  | 2 | 274 gm | 1.03 ml/kg | 0.3 ml | IM | 30 minutes |
| II (Quinine + Drug #1) | 3 | 286 gm | 1.03 ml/kg | 0.3 ml | IM | 24 hours |
|  | 4 | 283 gm | 1.03 ml/kg | 0.3 ml | IM | 24 hours |
| III (Quinine + Drug #2) | 5 | 291 gm | 4.86 ml/kg | 1.5 ml | Oral | 24 hours |
|  | 6 | 275 gm | 4.86 ml/kg | 1.4 ml | Oral | 24 hours |

TABLE II

| | ANALYTICAL RESULTS | |
|---|---|---|
| Group # | Plasma Sample # | Quinine (1) |
| I | 1 | 0.4 mcg/ml serum |
| II | 2 | none detected |
| III | 3 | 0.5 mcg/ml serum |

(1) Method detection limit is 0.1 mcg/ml.

Quinine was detected in Group I at a level of 0.4 mcg/ml and in Group III at a level of 0.5 mcg/ml. No quinine was found in Group II. The detection level of the method used is 0.1 mcg/ml. These data indicate that Drug No. 2 was effective in prolonging the residence time of quinine in mammals.

| The composition of Drug No. 3 was: | |
|---|---|
| Potassium Hydrogen Tartrate | 0.48 grams |
| Tannic Acid | 0.08 grams |
| Pectin | 0.94 grams |
| L-Tyrosine | 0.21 grams |
| Water to make 316 ml. | |

When 25 mg. of quinine dihydrochloride was dissolved in 2.5 ml of Drug No. 3, and injected IM into rats, the results of the quinine level in blood samples after 24 hours was the same as with Drug No. 2. When this procedure was repeated except that administration was by the oral route, the same results were obtained.

B. HUMAN STUDIES

The following data were obtained in human subjects at Baku, U.S.S.R.

Patients (about 65 kg of body weight) suffering from malaria were treated in the conventional way with quinine dihydrochloride. The blood levels 24 hours after the last oral administration of the drug (260 mg) showed almost no quinine in the blood plasma. When the quinine dosage was combined with 60 ml of Drug No. 2, and blood samples taken after 20 and 30 days after last administration, detectable amount of quinine were observed.

Patients (about 65 kg. of body weight) suffering from dysentery were treated with sulfathiazole 2.0 grams per day by oral route. After 48 hours, no drug was present in the blood plasma. When the drug was accompanied at each dosing with 60 ml of Drug No. 2, except that glutamic acid was substituted for L-tyrosine on an equal weight basis, the sulfathiazole could be detected in the plasma 30 days after date of the last dose.

The effective amount of the prolongating compositions, based on a body weight of 65 kg, is about 50 to 60 ml plus or minus 50% by volume.

The basic use of the prolongating compositions is to administer it at or very closely around the time of administering the active drug. This provides the prolongating effect. The active drug and the prolongating compositions can be administered in a variety of conventional ways, viz., I. V., I. M., oral, etc.

The present invention is applicable to the full range of sulfa drugs which are otherwise known as sulfonamides having bacteriostatic properties.

The cinchona alkaloids are a known class of antimalerial drugs. This invention is applicable to all of the antimalarial cinchona alkaloids including quinine sulfate, quinine dihydrochloride and quinacrine and its salts, known to those skilled in the art, the antimalarial cinchona alkaloids are often given in conjunction with other drugs such as pyrimethamine, the sulfonamides and sulfones. All such combinations are contemplated by the present invention.

Having fully described the invention it is intended that it be limited only by the lawful scope of the appended claims.

I claim:

1. A composition adapted to prolong the residence time of drugs in the circulating plasma of mammals including humans comprising about 48 parts by weight potassium hydrogen tartrate, about 8 parts by weight tannic acid, about 94 parts by weight pectin, about 21 parts by weight L-tyrosine, about 6 parts by weight hexanoic acid, and about 200 parts by weight 10% riboflavin.

2. The composition of claim 1 in the form of an aqueous solution.

3. The composition of claim 1 containing an effective amount of cinchona alkaloid drug.

4. The method of treating malaria which comprises administering to a mammal suffering malaria a composition comprising an effective amount of a cinchona alkaloid drug in combination with a composition adapted to prolong the residence time of drugs in the circulating plasma of mammals including humans comprising about 48 parts by weight potassium hydrogen tartrate, about 8 parts by weight tannic acid, about 94 parts by weight pectin, about 21 parts by weight L-tyrosine, about 6 parts by weight hexanoic acid, and about 200 parts by weight 10% riboflavin.

* * * * *